United States Patent
Gliner

(12) 
(10) Patent No.: US 6,671,557 B1
(45) Date of Patent: Dec. 30, 2003

(54) SYSTEM AND METHOD FOR PROVIDING PERCUTANEOUS ELECTRICAL THERAPY

(75) Inventor: Brad Gliner, Sammamish, WA (US)

(73) Assignee: Meagan Medical, Inc., Reno, NV (US)

( * ) Notice: Subject to any disclaimer, the term of this patent is extended or adjusted under 35 U.S.C. 154(b) by 360 days.

(21) Appl. No.: 09/686,993

(22) Filed: Oct. 10, 2000

(51) Int. Cl.$^7$ ................................................ A61N 1/18
(52) U.S. Cl. ............................ 607/46; 607/69; 607/73; 607/2
(58) Field of Search .............................. 607/53, 68, 69, 607/46, 70–74, 45, 2

(56) References Cited

U.S. PATENT DOCUMENTS

| | | |
|---|---|---|
| 2,864,371 A | 12/1958 | Parodi |
| 3,030,959 A | 4/1962 | Grunert |
| 3,090,151 A | 5/1963 | Stewart et al. |
| 3,208,452 A | 9/1965 | Stern |
| 3,938,526 A | 2/1976 | Anderson et al. |
| 3,943,935 A | 3/1976 | Cameron |
| 3,983,881 A | 10/1976 | Wickham ..................... 128/421 |
| D249,550 S | 9/1978 | Jankelson et al. |
| 4,139,011 A | 2/1979 | Benoit et al. |
| 4,153,059 A * | 5/1979 | Fravel et al. ............... 128/422 |
| 4,207,903 A | 6/1980 | O'Neill |
| 4,256,116 A | 3/1981 | Meretsky et al. ........... 128/421 |
| 4,262,672 A | 4/1981 | Kief |
| 4,281,659 A | 8/1981 | Farrar et al. |
| 4,284,056 A * | 8/1981 | Sugasawa ................ 179/197 E |
| 4,381,012 A | 4/1983 | Russek |
| 4,408,617 A | 10/1983 | Auguste |
| 4,431,000 A | 2/1984 | Butler et al. ................. 128/421 |
| 4,437,467 A | 3/1984 | Helfer et al. |
| 4,512,351 A | 4/1985 | Pohndorf |
| 4,541,432 A * | 9/1985 | Molina-Negro et al. .... 128/421 |
| 4,556,064 A | 12/1985 | Pomeranz et al. ....... 128/423 R |
| 4,583,549 A | 4/1986 | Manoli |
| 4,685,466 A | 8/1987 | Rau |
| 4,686,996 A | 8/1987 | Ulbrich |
| 4,712,558 A | 12/1987 | Kidd et al. .................. 128/421 |
| D297,047 S | 8/1988 | Hon et al. |
| 4,765,310 A | 8/1988 | Deagle et al. |
| D299,747 S | 2/1989 | Wilson et al. |
| 4,895,154 A | 1/1990 | Bartelt et al. |
| 4,934,371 A | 6/1990 | Malis et al. |
| 4,949,734 A | 8/1990 | Bernstein |
| 4,953,564 A | 9/1990 | Berthelsen |
| 4,979,508 A * | 12/1990 | Beck ....................... 128/419 R |

(List continued on next page.)

FOREIGN PATENT DOCUMENTS

| | | |
|---|---|---|
| FR | 2 500 309 | 8/1982 |
| FR | 2 500 745 | 9/1982 |
| GB | 2 163 355 A | 7/1985 |
| GB | 2 255 719 A | 5/1991 |

OTHER PUBLICATIONS

U.S. patent application Ser. No. 09/451,547, Bishay et al., filed Dec. 1, 1999.

(List continued on next page.)

*Primary Examiner*—Mark Paschall
(74) *Attorney, Agent, or Firm*—Perkins Coie LLP

(57) ABSTRACT

A system and method for providing percutaneous electrical nerve stimulation therapy to a patient renders the therapy effective for a large patient population and a broad range of patient conditions. The method includes the steps of inserting an electrode into the patient and applying an electrical signal between the electrode and the patient's body at a plurality of frequencies that automatically vary over the range of frequencies. The range of frequencies may have a minimum frequency of at most about 20 Hz and a maximum frequency of at least about 40 Hz. In addition, the electrical signal may be compensated for changes in frequency. The compensation may be in the form of amplitude adjustment or pulse with adjustment to provide effective signal energy over the entire range of applied frequencies.

81 Claims, 6 Drawing Sheets

U.S. PATENT DOCUMENTS

| | | | |
|---|---|---|---|
| 5,012,811 A | 5/1991 | Malis et al. | |
| D318,330 S | 7/1991 | Doty et al. | |
| 5,036,850 A | 8/1991 | Owens | |
| 5,054,486 A | 10/1991 | Yamada | |
| 5,094,242 A | 3/1992 | Gleason et al. | |
| 5,117,826 A | 6/1992 | Bartelt et al. | |
| 5,207,231 A | 5/1993 | Fakhri | |
| 5,211,175 A | 5/1993 | Gleason et al. | |
| 5,246,014 A | 9/1993 | Williams et al. | |
| 5,255,691 A | 10/1993 | Otten | |
| 5,269,304 A | 12/1993 | Matthews | |
| 5,281,218 A | 1/1994 | Imran | |
| 5,332,401 A | 7/1994 | Davey et al. | |
| D357,069 S | 4/1995 | Plahn et al. | |
| 5,417,719 A | 5/1995 | Hull et al. | |
| 5,423,314 A | 6/1995 | Schmid | |
| 5,439,440 A | 8/1995 | Hofmann | |
| 5,449,378 A | 9/1995 | Schouenborg | |
| 5,593,429 A | 1/1997 | Ruff | |
| 5,649,936 A | 7/1997 | Real | |
| 5,682,233 A | 10/1997 | Brinda | |
| 5,702,359 A | 12/1997 | Hofmann et al. | |
| 5,810,762 A | 9/1998 | Hofmann | |
| 5,840,057 A | 11/1998 | Aloisi | |
| 5,851,223 A * | 12/1998 | Liss et al. | 607/46 |
| 5,861,015 A | 1/1999 | Benja-Athon | |
| 5,873,849 A | 2/1999 | Bernard | |
| 5,891,182 A | 4/1999 | Fleming | |
| 5,928,144 A | 7/1999 | Real | |
| 5,941,845 A | 8/1999 | Tu et al. | |
| 5,948,008 A | 9/1999 | Daikuzono | |
| 5,968,011 A | 10/1999 | Larsen et al. | |
| 5,968,063 A | 10/1999 | Chu et al. | |
| 6,009,347 A | 12/1999 | Hofmann | |
| 6,021,353 A | 2/2000 | Wang | |
| 6,032,064 A | 2/2000 | Devlin et al. | |
| 6,035,236 A | 3/2000 | Jarding et al. | 607/53 |
| 6,050,992 A | 4/2000 | Nichols | |
| 6,068,650 A | 5/2000 | Hofmann et al. | |
| 6,117,077 A | 9/2000 | Del Mar et al. | |
| 6,122,547 A | 9/2000 | Benja-Athon | |
| 6,208,893 B1 | 3/2001 | Hofmann | |
| 6,212,432 B1 | 4/2001 | Matsuura | |
| 6,219,569 B1 | 4/2001 | Kelly et al. | |
| D443,063 S | 5/2001 | Pisani et al. | |
| 6,236,890 B1 | 5/2001 | Oldham | |
| 6,269,270 B1 * | 7/2001 | Boveja | 607/45 |
| 6,304,785 B1 | 10/2001 | McCreery et al. | |
| 6,341,237 B1 | 1/2002 | Hurtado | |
| 6,355,021 B1 | 3/2002 | Nielsen et al. | |

OTHER PUBLICATIONS

U.S. patent application Ser. No. 09/451,795, Leonard et al., filed Dec. 1, 1999.

U.S. patent application Ser. No. 09/451,796, Leonard et al., filed Dec. 1, 1999.

U.S. patent application Ser. No. 09/451,799, Leonard et al., filed Dec. 1, 1999.

U.S. patent application Ser. No. 09/451,800, Bishay et al., filed Dec. 1, 1999.

U.S. patent application Ser. No. 09/452,477, Bishay et al., filed Dec. 1, 1999.

U.S. patent application Ser. No. 09/452,508, Leonard et al., filed Dec. 1, 1999.

U.S. patent application Ser. No. 09/452,510, Bishay et al., field Dec. 1, 1999.

U.S. patent application Ser. No. 09/452,663, Bishay et al., filed Dec. 1, 1999.

U.S. patent application Ser. No. 09/666,931, Leonard et al., filed Sep. 21, 2000.

U.S. patent application Ser. No. 09/667,183, Leonard, filed Sep. 21, 2000.

U.S. patent application Ser. No. 29/130,210, Leonard et al., filed Sep. 28, 2000.

Ahmed H. et al. "Percutaneous Electrical Nerve Stimulation (PENS): A Complementary Therapy for the Management of Pain Secondary to Bony Metastasis", The Clinical Journal of Pain (Dec. 1998) vol. 14, No. 4, pp. 320–323, Lippincott Williams & Wilkins, Philadelphia.

Ahmed H. et al. "Percutaneous Electrical Nerve Stimulation: An Alternative to Antiviral Drugs for Acute Herpes Zoster," Anesthesia & Analgesia (Oct. 1998) 87: 911–4.

Ballegaard, S. et al. "Acupuncture and Transcutaneous Electric Nerve Stimulation in the Treatment of Pain Associated with Chronic Pancreatitis. A Randomized Study", Scand. J. Gastroenterol. (Jun. 1985) 20: 1249–54.

Balogun, J. et al. "The effects of acupuncture, electroneedling and transcutaneous electrical stimulation therapies on peripheral haemodynamic functioning", Disability and Rehabilitation (Feb. 1998) vol. 20, No. 2, pp. 41–48, Taylor & Francis Ltd.

BD Microtainer Brand Safety Flow Lancet—Product No. 366356. BD catalog 1997–2000, http://catalog.bd.com/sctipts/OBDsheet.exe?FNC=productlist_Alistproducts_html_366356 (Aug. 2001), 3 pages.

BD Safety Products. BD Vacutainer Safety–Lok Blood Collection Set; BD Vacutainer SafetyGlide Blood Collection Assembly and BD Vacutainer Eclipse Blood Collection Needle, 1 page.

BD Vacutainer SafetyGlide Blood Collection Assembly. Quick Reference Card (Oct. 1999), 1 page.

Bushnell M. C. et al. "Electrical stimulation of peripheral and central pathways for the relief of musculoskeletal pain", Can. J. Physiol. Pharmacol. (May 1991) 69:697–703.

Cheng R., Pomeranz, B. "Electroacupuncture analgesia could be mediated by at least two pain–relieving mechanisms: endorphin and non–endorphin systems", Life Sciences (Dec. 1979) 25: 1957–62, Pergamon Press Ltd.

Cheng R. et al. "Electrocupuncture elevates blood cortisol levels in naive horses; sham treatment has no effect", Intern. J. Neuroscience (Feb. 1980) vol. 10, pp. 95–97, Gordon and Breach Science Publishers, Inc., Great Britain.

Cheng R. S. S., Pomeranz, B. "Electrotherapy of Chronic Musculoskeletal Pain: Comparison of Electroacupuncture and Acupuncture–Like Transcutaneous Electrical Nerve Stimulation", The Clinical Journal of Pain (1987) vol. 2, No. 3, pp. 143–149, Raven Press, New York.

Empi Eclipse+ Dual Channel Transcutaneous Electrical Nerve Stimulator User's Manual, Empi, Inc. (Sep. 1998), U.S. patent #D282,968, 31 pages.

Empi EPIX VT Dual Channel Transcutaneous Electrical Nerve Stimulator Instruction Manual, Empi, Inc. (1997) 22 pages.

Empi EPIX XL Tens Instruction Manual, Empi, Inc. (Sep. 1998) 22 pages.

Empi, Our Products: Electrotherapy for Rehabilitation, htt://www.empi.com/b/b2.htm, (Mar. 2001), 8 pages.

Gadsby, G. et al. "Nerve stimulation for low back pain—a review," Nursing Standard (Jul. 1997) vol. 11, No. 43, pp. 32–33.

Ghoname, E. et al. "Does the Stimulus Frequency Affect the Analgesic Response to Electrical Stimulation?" Anesthesia & Analgesia (Nov. 1999) 88: S210, Lippincott Williams & Wilkins.

Ghoname, E. et al. "Percutaneous Electrical Nerve Stimulation for Low Back Pain", JAMA (Mar. 1999) vol. 281, No. 9, pp. 818–823.

Ghoname, E. et al. "Percutaneous electrical nerve stimulation: an alternative to TENS in the management of sciatica", Pain (Nov. 1999) 83: 193–9, Elsevier Science B.V.

Ghoname, E. et al. "The Effect of Stimulus Frequency on the Analgesic Response to Percutaneous Electrical Nerve Stimulation in Patients with Chronic Low Back Pain", Anesthesia & Analgesia (Oct. 1999) 88: 841–6.

Ghoname, E. et al. "The Effect of the Duration of Electrical Stimulation on the Analgesic Response", Anesthesia & Analgesia (Jan. 1999) 88: S211.

Hamza, M. et al. "Effect of the Duration of Electrical Stimulation in Patients with Low Back Pain", Anesthesiology (Dec. 1999), vol. 91, No. 6, pp. 1622–1627, Lippincott Williams & Wilkins, Inc.

Healthronics HANS LY257 User Manual, Healthronics Pte Ltd., Singapore, 15 pages.

Innovative Healthcare: Electrotherapy Pain & Rehabilitation Product Solutions from Rehabilicare. [Includes product description of SporTX and Ortho DX], http://www.mvp-design.com/sites/rehabilicare/all_products.html, (Aug. 2001), 3 pages.

Intelect Legend Stim Clinical Reference Manual, vol 4, Intelect Legend Series, Chattanooga Group, Inc., 25 pages.

Landau, B. et al. "Neuromodulation Techniques for Medically Refractory Chronic Pain", Annu. Rev. Med. (Feb. 1993) 44: 279–87, Annual Reviews Inc.

Lehmann T. et al. "Efficacy of Electroacupuncture and TENS in the Rehabilitation of Chronic Low Back Pain Patients", Pain (Sep. 1986) 26: 277–90, Elsevier Science Publishers B.V.

Model AWQ–104B Multi–Purpose Electronic Acupunctoscope Instruction Manual, 10 pages.

Pointer F–3 Instruction Manual, ITO Co., Ltd., Tokyo, Japan (1999), 12 pages.

Radionics products brochure. "A Significant Breakthrough Using Pulsed Radiofrequency for Pain Management", includes RF Lesion Generator System, Model RFG–3C Plus, (1997), Radionics, Burlington, MA, 10 pages.

Rehabilicare Ortho Dx product brochure. "Reduce Rehabilitation Time and Enhance Patient Comfort with Ortho Dx", Rehabilicare, New Brighton, MN, 2 pages.

Rehabilicare SMP–plus product brochure. "SMP–plus. The Pain Relief Solution for Hard to Treat Patients", Rehabilicare, New Brighton, MN (1999) 2 pages.

Rehabilicare SporTX Product Data Sheet, 1 page.

Rehabilicare SporTX Quick Set–Up Instruction, "SPORTX. Get back in the Game!", Rehabilicare, New Brighton, MN, 2 pages.

Ulett, G. et al. "Electroacupuncture: Mechanisms and Clinical Application", Biological Psychiatry (Jul. 1998) 44: 129–38.

White, P. et al. "Percutaneous Neuromodulation Therapy: Does the Location of Electrical Stimulation Effect the Acute Analgesic Response?" Anesthesia & Analgesia (Oct. 2000) 91: 1–6.

White, P. et al. "The Effect of Montage on the Analgesic Response to Percutaneous Neuromodulation Therapy" Anesthesia & Analgesia (Feb. 2001) 92: 483–7.

PCT International Search Report for International Application No. PCT/US01/31441; mailed May 7, 2002; Applicant: Vertis Neuroscience, Inc., 8 pages.

Cramp AF, Gilsenan C, Lowe AS, Walsh DM. The effect of high– and low–frequency transcutaneous electrical nerve stimulation upon cutaneous blood flow and skin temperature in healthy subjects. Clin Physiol. 2000; 20:150–7.

Galletti SP, Bergamini M, Pantaleo T. [Hightlights in the subject of low frequency–high intensity TENS (review)]. Minerva Stomatol. 1995; 44:421–9.

Ghoname ES, Craig WF, White PF, et al. The effect of stimulis frequency on the analgesic response to percutaneous electrical nerve stimulation in patents with chronic low back pain [see comments]. Anesth Analg. 1999; 88:841–6.

Hamza MA, White PF, Ahmed He, Ghoname EA. Effect of the frequency of transcutaneous electrical nerve stimulation on the postoperative opioid analgesic requirement and recovery profile. Anesthesiology. 1999; 91:1232–8.

Han JS, Chen XH, Sun SL, et al. Effect of low– and high–frequency TENS on Met–enkephalin–Arg–Phe and dynorphin A immunoreactivity in human lumbar CSF. Pain. 1991; 47:295–8.

Liss S. Liss B. Physiological and therapeutic effects of high frequency electrical pulses. Integr Physiol Behav Sci. 1996; 31:88–95.

Marchand S, Bushnell MC, Duncan GH. Modulation of heat pain perception by high frequency transcutaneous electrical nerve stimulation (TENS). Clin J Pain. 1991; 7:122–9.

Romita VV, Suk A, Henry JL. Parametric studies on electroacupuncture–like stimulation in a rat model: effects of intensity, frequency, and duration of stimulation on evoked antinociception. Brian Res Bull. 1997; 42:289–96.

Rooney JG, Currior DP, Nitz AJ. Effect of variation in the burst and carrier frequency modes of neuromuscular electrical stimulation on pain perception of healthy subjects [published erratum appears in Phys Ther 1993 Feb; 73(2):128]. Phys Ther. 1992; 72:800–6; discussion 807–9.

Sluka KA, Bailey K, Bogush J, Olson R, Ricketts A. Treatment with either high or low frequency TENS reduces the secondary hyperalgesia observed afer injection of kaolin and carrageenan into the knee joint. Pain. 1998; 77–97:102.

Somers DL, Clemente FR. High–frequency transcutaneous electrical nerve stimulation alters thermal but not mechanical allodynia following chronic constriction injury of the rat sciatic nerve. Arch Phys Med Rehabil. 1998; 79:1370–6.

Starpbinet M, Volkova LD. [Analgesic effect of high–frequency and acupuncture–like transcutaneous electric stimulation of nerve fibers in spinal osteochondrosis]. Zh Nevropaatol Psikhiatr Im S S Korsakova. 1985; 85:350–4.

Van Doren CL. Contours of equal perceived amplitude and equal perceived frequency for electrocutaneous stimuli. Percept Psychophys. 1997; 59:613–22.

Almay BG, Johansson F, von Knoring L, Sakurada T, Terenious L. Long–term high frequency transcutaneous electrical nerve stimulation (hi–TNS) in chronic pain. Clinical response and effects on CSF—endorphins, monoamine metabolites, substance P–like immunoreactivity (SPLI) and pain measures. J Psychosom Res. 1985; 29:247–57.

Katims JJ, Long DM, Ng LK. Transcutaneous nerve stimulation. Frequency and waveform specificity in humans. Appl Neurophysiol. 1986; 49:86–91.

Johnson MI, Ashton CH, Thompson JW. An in–depth study of long term users of transcutaneous electrical nerve stimulation (TENS). Implications for clinical use of TENS. *Pain.* 1991; 44:221–9.

Gopalkrishnann P, Sluka KA. Effect of Varying Frequency, Intensity, and Pulse Duration of Transcutaneous Electrical Nerve Stimulation on Primary Hyperalgesia in Inflamed Rats. *Arch Phys Med Rehabil.* 2000; 81:984–990.

O'Brien WJ, Rutan FM, Sanborn C. Omer GE. Effect of Transcutaneous Electrical Nerve Stimulation on Human Blood B–Endorphin Levels. *Physical Therapy.* 1984; 64:1367–1374.

Brull S, Silverman D. Pulse Width, Stimulus Intensity, Electrode Placement, and Polarity During Assessment of Neuromuscular Block. *Anesthesiology.* 1995; 83:702–709.

Baker L, Bowman B, McNeal D. Effects of Waveform on Comfort During Neuromuscular Electrical Stimulation. *Clinical Orthopaedics and Related Research.* 1988; 233:75–85.

Cassuto J, Liss S, Bennett A. The use of modulated energy carried on a high frequency wave for the relief of intractable pain. *Int. J. Clin. Pharm. Res.* XIII(4) 239–241 (1993).

Foster N, Baxter F, Walsh D., et al. Manipulation of Transcutaneous Electrical Nerve Stimulation Variables Has No Effect on Two Models of Experimental Pain in Humans. *The Clinical Journal of Pain.* 1996; 12:301–310.

Gracanin F, Trnkoxzy A. Optimal Stimulus Parameters for Minimum Pain in the Chronic Stimulation of Innervated Muscle. *Arch Phys Med Rehabil.* 19975; 56:243–249.

Jette D. Effect of Different Forms of Transcutaneous Electrical Nerve Stimulation on Experimental Pain. *Physical Therapy.* 1986; 66:2;187–193.

Johnson MI, Ashon CH, et al. Analgesic effects of different frequencies of transcutaneous electrical nerve stimulation on cold–induced pain in normal subjects. *Pain.* 1989; 39:231–236.

Johnson MI, Ashton CH, et al. Analgesic effects of different pulse patterns of transcutaneous electrical nerve stimulation on cold–induced pain in normal subjects. *Journal of Psychosomatic Research.* 1991; 35:2/3; 313–321.

Leem J, Park E, Paik K. Electrophysiological evidence for the antinociceptive effect of transcutaneous electrical stimulation on mechanically evoked responsiveness of dorsal horn neurons in neuropathic rats. *Neuroscience Letters.* 1995;192:197–200.

Moreno–Aranda J, Seireg A. Electrical Parameters for over–the–skin muscle stimulation. *J. Biomechanics.* 1981; 14:9; 579–585.

Moreno–Aranda J, Seireg A. Investigation of over–the–skin electrical stimulation parameters for different normal muscles and subjects. *J. Biomechanics.* 1981; 14:9; 587–593.

Omura Y, et al. Basic electrical parameters for safe and effective electro–therapeutics (electro–acupuncture, tes, tenms (or tems), tens and electro–magnetic field stimulation with or without drug field) for pain, neuromuscular skeletal problems, and circulatory disturbances. *Acupuncture & Electro–Therapeutics Res., Int. J.* 1987; 12:201–225.

Omura Y. Electrical parameters for safe and effective electro–acupuncture and transcutaneous electrical stimulation: threshold potentials for tingling, muscle contraction and pain; and how to prevent adverse effects of electro–therapy. *Acupuncture & Electro–Therapeutics Res., Int. J.* 1985; 10:335–337.

Ordog G. Transcutaneous Electrical Nerve Stimulation versus Oral Analgesic: A Randomized Double–blind Controlled Study in Acute Traumatic Pain. *American Journal of Emergency Medicine.* 1987;; 5:1; 6–10.

Balogun J. Effects of ramp time on sensory, motor and tolerance thresholds during exogenous electrical stimulation. *The Journal of Sports Medicine and Physical Fitness.* 1991; 3:4; 521–526.

AAMI Neurosurgery Committee; AAMI Implantable Neurostimulator Subcommittee. Implantable peripheral nerve stimulators. *Association for the Advancement of Medical Instrumentation.* NS15–1995; cover–8.

EPIX XLI TENS Instruction Manual, *Empi, Inc.*, 1988.

Carroll D, Tramer M, McQuay H, Nye B, Moore A. Randomization is important in studies with pain outcomes: systematic review of transcutaneous electrical nerve stimulation in acute postoperative pain. *Br J Anaesth.* 1996; 77:798–803.

* cited by examiner

SYSTEM AND METHOD FOR PROVIDING PERCUTANEOUS ELECTRICAL THERAPY

FIELD OF THE INVENTION

The present invention is generally directed to a system and method for providing percutaneous electrical nerve stimulation therapy. The present invention is more particularly directed to such a system and method capable of providing effective treatment to a large patient population automatically without requiring individual therapy tailoring or adjustment for each patient.

BACKGROUND OF THE INVENTION

Electrical therapy has long been used in medicine to treat pain and other conditions. One such therapy is transcutaneous electrical nerve stimulation (TENS). This therapy involves the delivery of electrical energy through patch electrodes placed on the surface of a patient's skin to treat pain in tissue beneath and around the location of the patch electrodes. The electrical energy is typically delivered to the patient in a waveform that varies according to a single preset frequency or to a limited frequency combination.

The relationship between waveform frequency and efficacy varies from patient to patient and from condition to condition. Prior art TENS studies therefore vary greatly in their conclusions regarding the efficacy of different TENS waveforms. For example, a review of 46 published TENS studies showed a wide variation in pain relief effect. It is difficult (if not impossible) to determine from these studies which waveform frequency should be used to treat a new patient or a prior patient with a new condition.

Some studies have attempted to determine the relationship between waveform frequency and the mechanism underlying the therapeutic effect, such as pain relief. For example, one study of 37 patients determined that TENS applied at a relatively low frequency (2 Hz) increased the concentration of an enkaphalin pain reliever in patients' cerebral spinal fluid (CSF), while TENS applied at a relatively high frequency (100 Hz) increased the concentration of a dynorphin pain reliever in the CSF. These studies did not attempt to correlate the increased concentrations of these substances in the CSF with pain relief effect, nor did they suggest which patients would benefit more from one frequency or the other or which conditions were best treated at one frequency or the other.

Electrical therapy to treat pain and other conditions may also be delivered percutaneously. This percutaneous approach is commonly referred to as Percutaneous Neuromodulation Therapy (PNT) or Percutaneous Electrical Nerve Stimulation (PENS). Like the TENS studies, however, published studies describing percutaneous electrical therapy have focused on limited patient populations and on limited frequencies and frequency combinations. These studies do not guide clinicians in the treatment of any particular patient with unknown electrical therapy response characteristics and an unknown condition underlying the apparent symptoms.

Thus, a significant drawback of prior art electrical therapy approaches is their failure to provide a therapeutic regime that will be efficacious across entire populations of patients and across a variety of patient conditions. At best, prior art approaches require trial and error testing of the patient to determine which waveform frequency would be best to treat that patient's condition, thereby consuming scarce medical personnel time and delaying the possible therapeutic effect for the patient. At worst, the prior art electrical therapy systems take a "one size fits all" treatment approach with widely varying results.

It is therefore an object of this invention to provide an electrical therapy system and method that maximizes efficacy across patient populations and patient conditions.

SUMMARY OF THE INVENTION

The present invention therefore provides a method of providing percutaneous electrical therapy to a patient, which renders the therapy effective for a large patient population and a broad range of patient conditions. The method includes the steps of inserting an electrode into the patient and applying an electrical signal between the electrode and the patient's body at a plurality of frequencies that automatically vary over a range having a minimum frequency of at most about 20 Hz and having a maximum frequency of at least about 40 Hz.

The electrical signal preferably includes a plurality of pulses with each consecutive pair of pulses being separated by an interpulse interval. The interpulse intervals may be automatically varied monotonically or randomly.

The method may further include the step of compensating the electrical signal for changes in frequency of the electrical signal. The compensation may be in the form of amplitude or pulse width adjustments to provide effective signal energy over the range of frequencies.

The present invention further provides a system for providing percutaneous electrical therapy to a patient. The system includes electrode means insertable into the patient and signal generating means for applying an electrical signal between the electrode means and the patient's body, the signal generating means including frequency varying means for applying the electrical signal between the electrode means and the patient's body at a plurality of frequencies that automatically vary over a range having a minimum frequency of at most about 20 Hz and having a maximum frequency of at least about 40 Hz.

The electrical signal preferably includes a plurality of biphasic pulses, each biphasic pulse including a consecutive pair of pulses, and each consecutive pair of biphasic pulses being separated by an interpulse interval. The frequency varying means may vary the interpulse intervals monotonically or randomly to automatically vary the frequency of the electrical signal.

The system may further include compensating means for compensating the electrical signal for changes in frequency of the electrical signal. The compensation may adjust amplitude or pulse width of the electrical signal to provide signal energy over the frequency range.

The present invention still further provides a system for providing percutaneous electrical therapy to a patient comprising at least one electrode insertable into the patient and a signal generator adapted to be coupled between the at least one electrode and the patient's body. The signal generator provides an electrical signal at a plurality of frequencies that automatically vary over a range having a minimum frequency of at most about 20 Hz and having a maximum frequency of at least about 40 Hz.

BRIEF DESCRIPTION OF THE DRAWINGS

The features of the present invention which are believed to be novel are set forth in the appended claims. The invention, together with further objects and advantages thereof, may best be understood by making reference to the following description taken in conjunction with the accompanying drawings, in the several figures of which like reference characters identifying identical elements, and wherein:

DETAILED DESCRIPTION OF THE PREFERRED EMBODIMENTS

Figure 1:
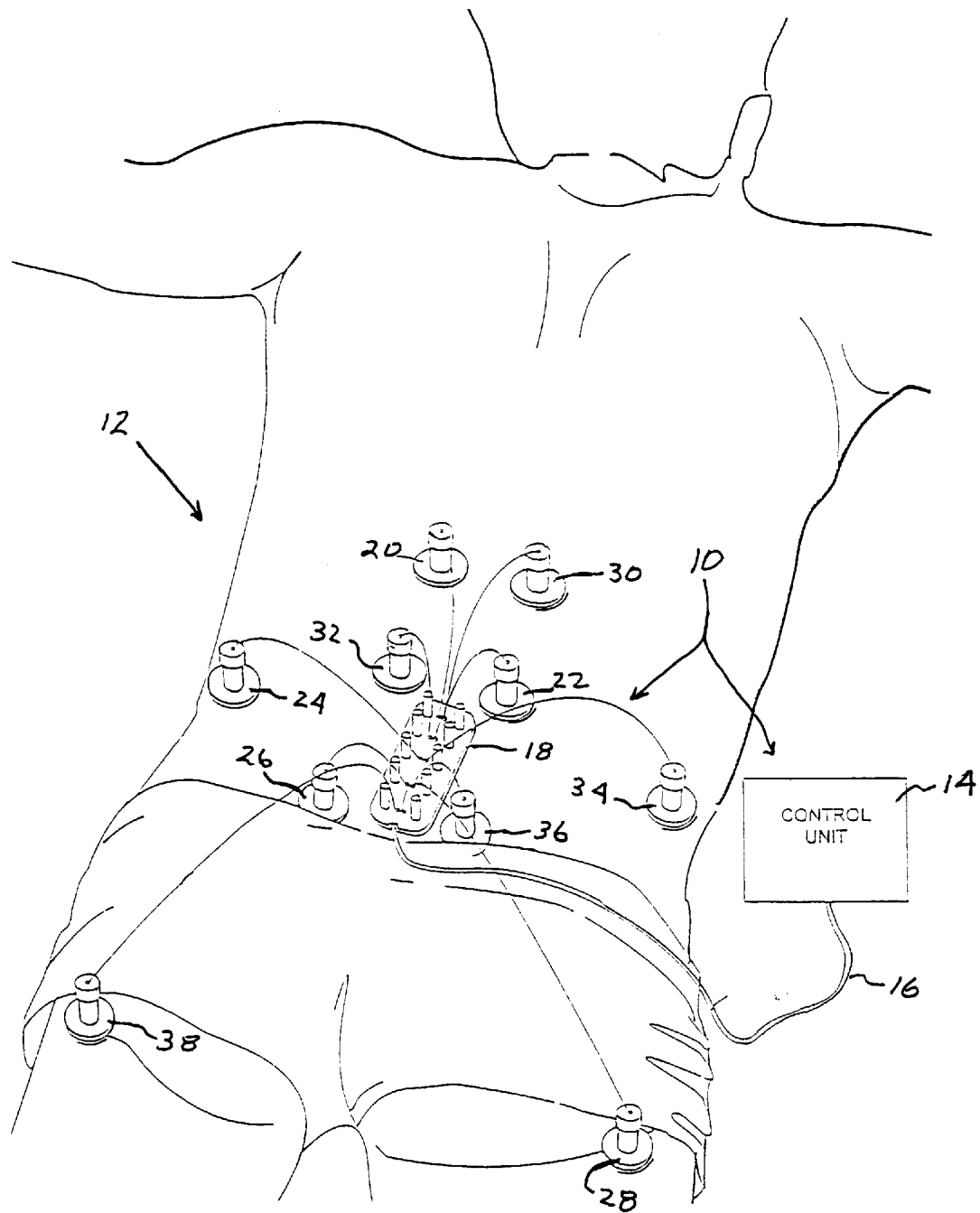
FIG. 1 shows a montage of electrodes and a control unit for treating low back pain of a patient with PENS in accordance with an embodiment of the present invention.

Referring now to FIG. 1, it illustrates a system 10 embodying the present invention for providing electrical therapy to a patient 12. Here, the patient is being treated for low back pain.

The system 10 includes a plurality of electrodes and a control unit 14. A first half of the electrodes including electrodes 20, 22, 24, 26, and 28 form cathode electrodes, and a second half of the electrodes including electrodes 30, 32, 34, 36, and 38 form corresponding anode electrodes. Each electrode includes a needle, which may be inserted into the patient's tissue. Once the electrodes are placed as shown, a therapeutic electrical signal is applied by the control unit 14 through a cable 16 and distributed between each cathode/anode electrode pair 20, 30; 22, 32; 24, 34; 26, 36; and 28, 38 by a tool tray 18. As will be appreciated by those skilled in the art, the number and placement of the electrodes and their designations as cathode or anode may be otherwise than as shown for treating a particular ailment without departing from the present invention.

In accordance with the broader aspects of the present invention, the control unit 14 automatically varies the frequency of the electrical signal applied to the electrodes over a comparatively wide range of frequencies having a minimum frequency of at most about 20 Hz and a maximum frequency of at least about 40 Hz. This will cause each of numerous therapeutic physiologic responses to be obtained from the applied signal as opposed to isolated physiologic responses obtained in the prior art through the use of a single or limited number of frequencies. Still further, since each individual has different physiologic response characteristics versus applied frequency, the automatically varying frequency of the electrical signal will cause the therapy to be effective for a large patient population not withstanding their different physiologic response characteristics. Perhaps most importantly, the automatically varying frequency eliminates the aforementioned trial and error and permits non-physician personnel to apply the therapy to each patient in a uniform manner and with effective results.

Figure 2:
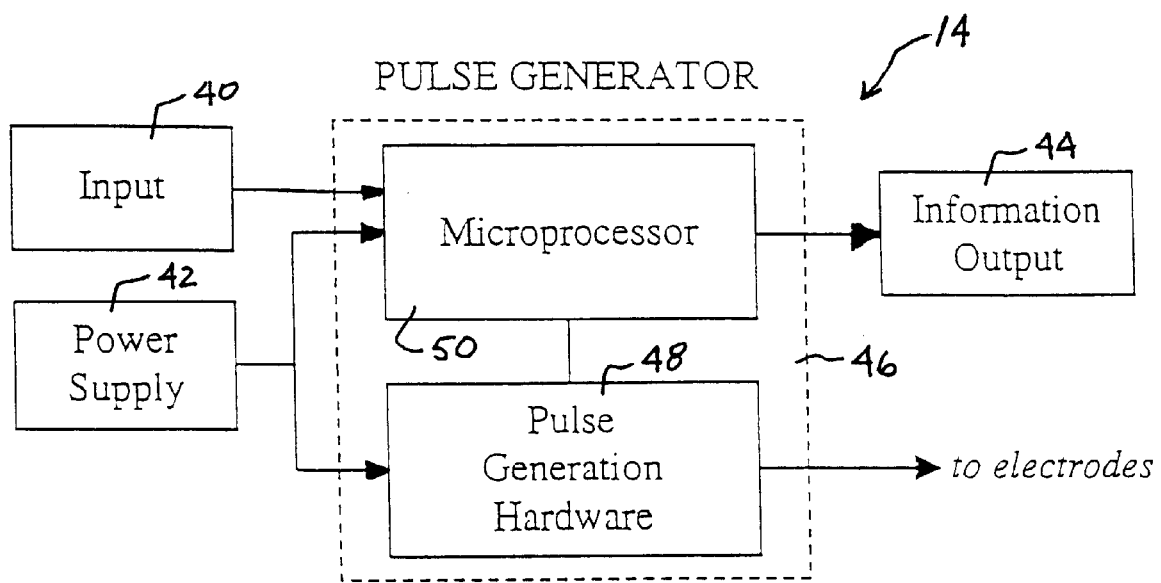
FIG. 2 is a schematic block diagram of the control unit of FIG. 1.

Referring now to FIG. 2, it illustrates a preferred embodiment of the control unit 14 in block diagram form. The control unit includes an input 40, a power supply 42, an information output 44, and a pulse generator 46. The pulse generator includes pulse generation hardware 48 and a microprocessor 50.

As will be seen hereinafter, the control unit 14 is capable of providing an electrical signal which automatically varies in frequency over a comparatively broad range of frequencies. As will also be seen hereinafter, the control unit may compensate the electrical signal according to the electrical signal frequency. The input 40, which may be a keypad or the like, provides selection of the electric signal frequency range, the manner in which the frequency is automatically varied in the selected range, and the manner in which the electrical signal is compensated.

The power supply 42 provides suitable operating voltage to the various active components of the control unit 14. It may be of a design well known in the art.

The information output 44 may be a liquid crystal display or the like. The information output 44 may be used to display the selected frequency range, the selected manner in which the frequency is automatically varied, and the selected manner in which the electrical signal is compensated with frequency.

Figure 4:
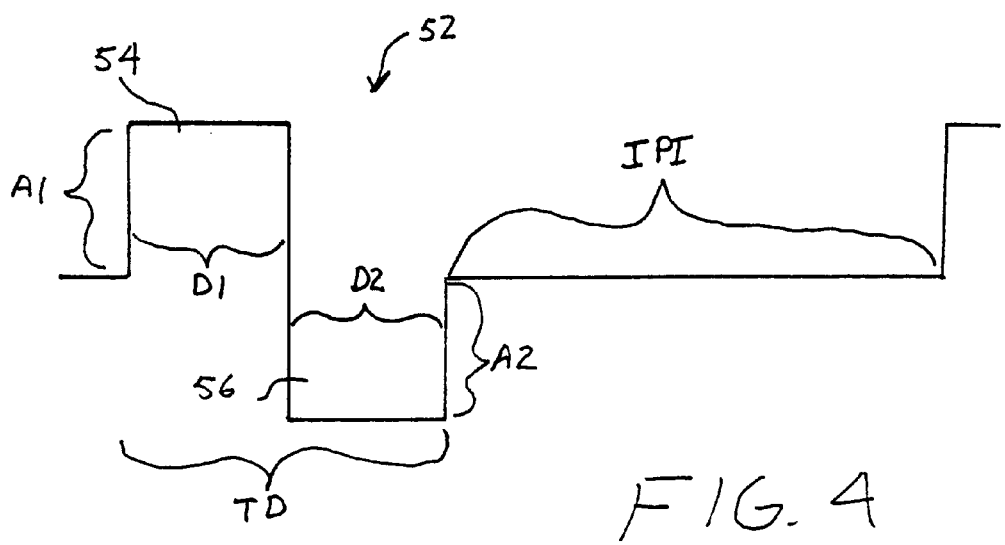
FIG. 4 is a waveform illustrating one complete cycle of an electrical signal which may be applied to the electrodes of FIG. 1 in accordance with a preferred embodiment of the present invention.

The pulse generation hardware 48 may be of the type well known in the art. It provides the electrical signal under control of the microprocessor 50. The electrical signal is preferably a series of biphasic pulses as shown in FIG. 4. Each biphasic pulse includes a consecutive pair of pulses including a first pulse 54 of one polarity and a second pulse of an opposite polarity. Each pulse 54 and 56 has a duration D1 and D2, respectively, which may be on the order of 200 microseconds. The durations D1 and D2 may be equal as illustrated or may be different. Further the durations D1 and D2 result in a total pulse duration TD which, as will be seen hereinafter, may be varied with frequency as one manner of compensating the electrical signal.

Each of the pulses 54 and 56 further has an amplitude A1 and A2, respectively. The amplitudes A1 and A2 may also be different but preferably are equal as illustrated with a typical value between about 2 and 5 milliamperes and a maximum value between about 10 and 15 milliamperes, for example. As will be seen hereinafter, the amplitudes A1 and A2 may be varied with frequency as a preferred manner of compensating the electrical signal with frequency.

Finally, the biphasic pulses are separated by an interpulse interval IPI. The IPI alone may be varied by the control unit 14 for automatically varying the frequency of the electrical signal. When the total pulse duration TD is varied to compensate the electrical signal, the IPI is then varied in concert with the TD to obtain the desired adjustments in the electrical signal frequency.

Figure 3:
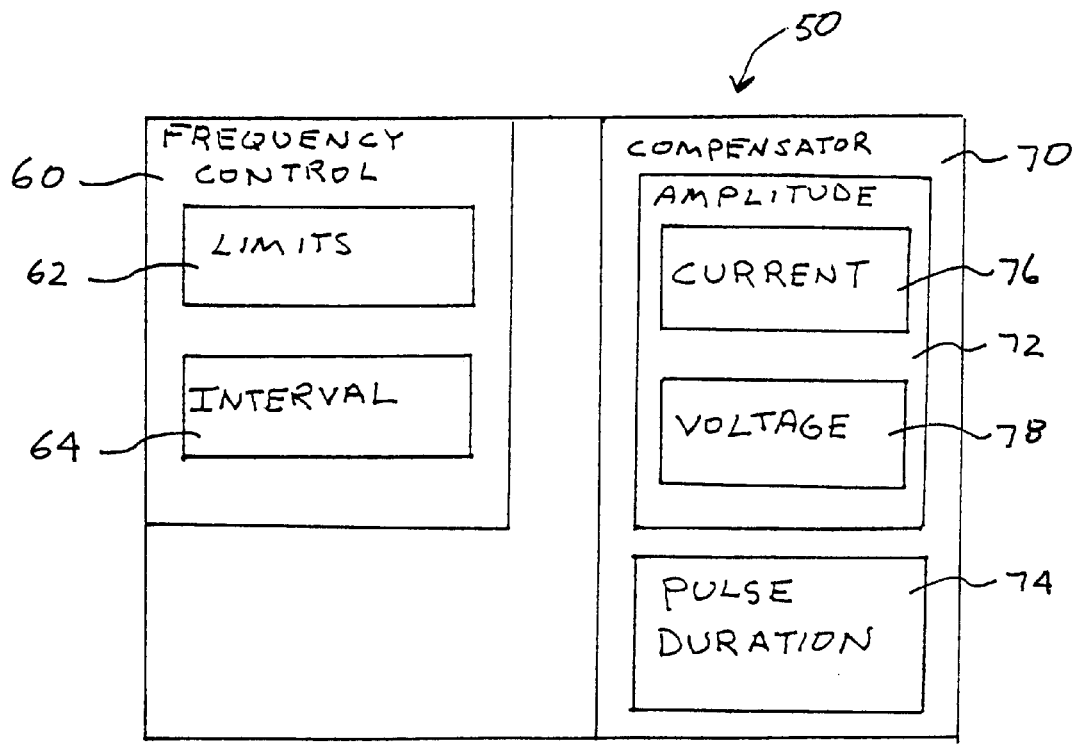
FIG. 3 is a more detailed representation of the microprocessor of the control unit of FIG. 2.

FIG. 3 shows the microprocessor 50 of FIG. 2 in greater detail. In a conventional manner, the microprocessor executes operating instructions, which it fetches from a memory (not shown) to provide its desired functionality in controlling the electrical signal applied to the electrodes. In doing so, the microprocessor 50 implements a plurality of functional stages, which may be divided into two groups of functional stages including frequency control stages 60 and compensator stages 70. The frequency control stages 60 include a limits stage 62 and an interval control stage 64. The compensator stages 70 include an amplitude control stage 72 and a pulse duration control stage 74. The amplitude control stage 72, as shown, includes substages including a current amplitude control stage 76 and a voltage amplitude control stage 78.

The limits stage 62, responsive to commands from the input 40, sets the frequency range of the electrical signal. The interval control stage 64 in turn varies the IPI automatically to automatically vary the frequency of the electrical signal. The manner in which the interval control stage 64 varies the frequency is selectable from the input 40. For example, the frequency may be increased and decreased monotonically across the frequency range or varied randomly. The general frequency range previously referred to may be augmented so that, for example, the minimum frequency is at most about 4 Hz while the maximum frequency is at least 50 Hz, the minimum frequency is at most about 2 Hz while the maximum frequency is at least about 100 Hz, or the minimum frequency is at most about 2 Hz and the minimum frequency is at most about 200 Hz.

The IPI may be varied with each biphasic pulse or varied at less frequent intervals in a predetermined manner so that the IPI's of a portion or multiple portions of the electrical signal are held constant. It may be varied monotonically or randomly in a repeated manner. Preferably the IPI is varied frequently enough so that a multitude of different frequencies, at least seven, are generated during a therapy session.

The compensator stage 70 compensates the electrical signal with frequency to maintain effective signal energy for each frequency of application. With a constant total duration (TD) and amplitude, the amount of applied electrical energy per unit time and consequently the perceived intensity of the stimulation will be directly related to frequency. Hence, higher frequencies will cause more energy per unit time to be applied than at lower frequencies. To compensate for this, and to provide effective signal energy per unit time for each applied frequency, the compensator 70, under control of input 40, may adjust the current amplitude of the electrical signal with frequency with stage 76, the voltage amplitude of the electrical signal with frequency with stage 78, or the total pulse duration (TD) with frequency with stage 74. Preferably, the amplitude and TD are varied in an inverse relation with frequency to maintain effectively applied energy per electrical signal cycle.

Figure 5:
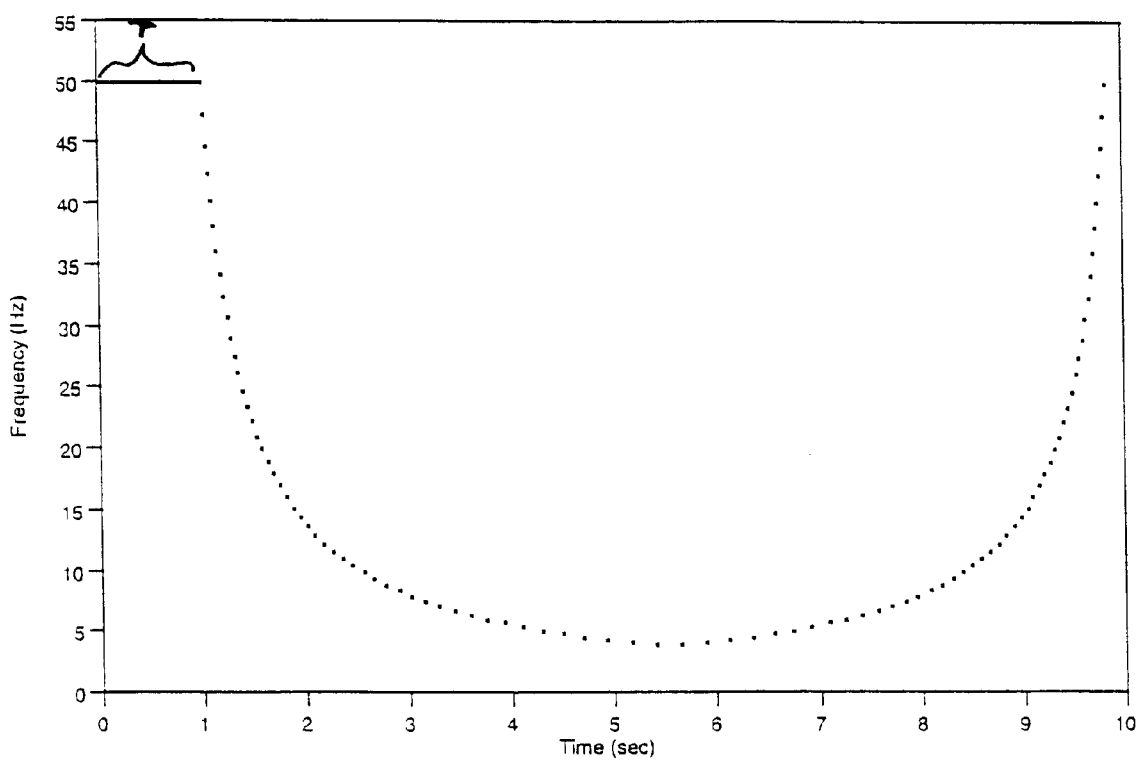
FIG. 5 is a plot of electrical signal frequency versus time illustrating the manner in which the frequency of the electrical signal may be automatically varied in accordance with a preferred embodiment of the present invention.

Referring now to FIG. 5, it illustrates a manner in which an electrical signal may be varied over time. It will be noted that during an initial time T the electrical signal frequency dwells or is held constant at an upper limit. This allows the patient to feel a massage-like movement for a brief period before the frequency begins to vary. Here, the frequency is decreased monotonically and then is increased monotonically. Preferably, at the end of the session, the frequency of the electrical signal is once again held at the upper frequency limit for a few seconds so that the patient leaves with a positive impression.

Figure 6:
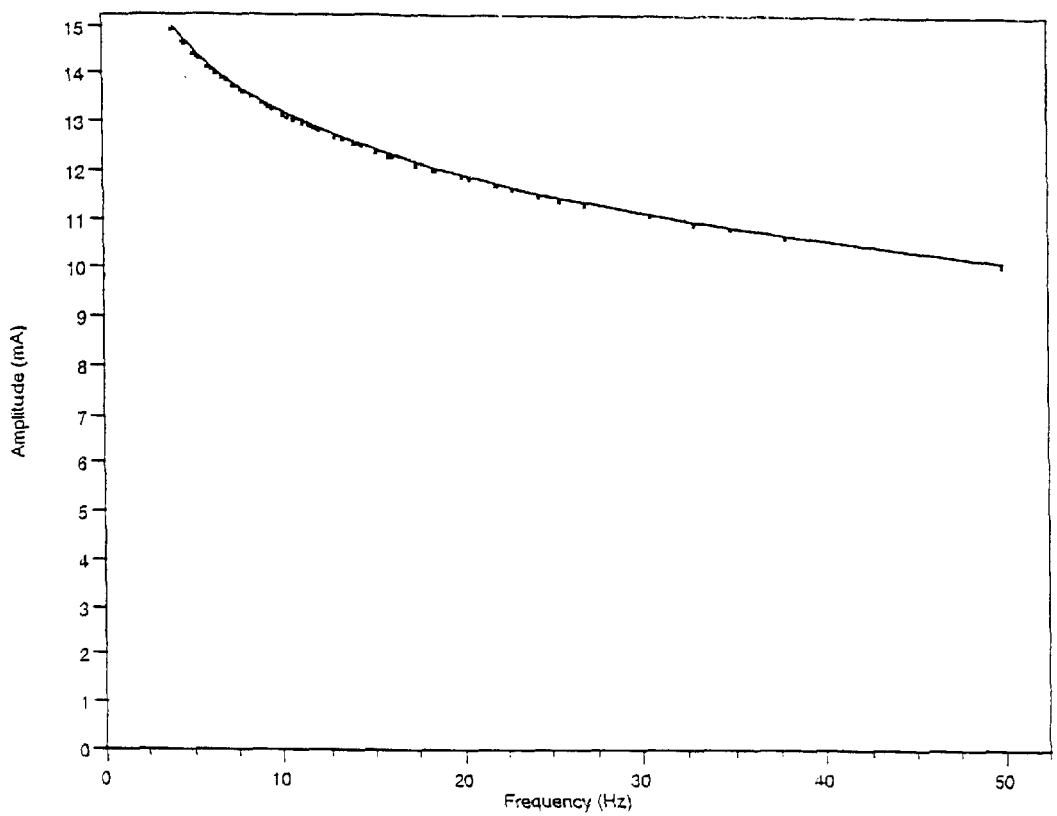
FIG. 6 is a plot illustrating the manner in which the electrical signal pulse amplitude may be varied with electrical signal frequency in accordance with the preferred embodiment of the present invention.

FIG. 6 illustrates how the pulse amplitude of the electrical signal represented in FIG. 5 may be adjusted with frequency. The relationship illustrated is adjustment in current in accordance with the formula:

$$I = C_1 - C_2 \log(F)$$

wherein, $C_1$ and $C_2$ are constants, and

F is the frequency of the electrical signal.

Figure 7:
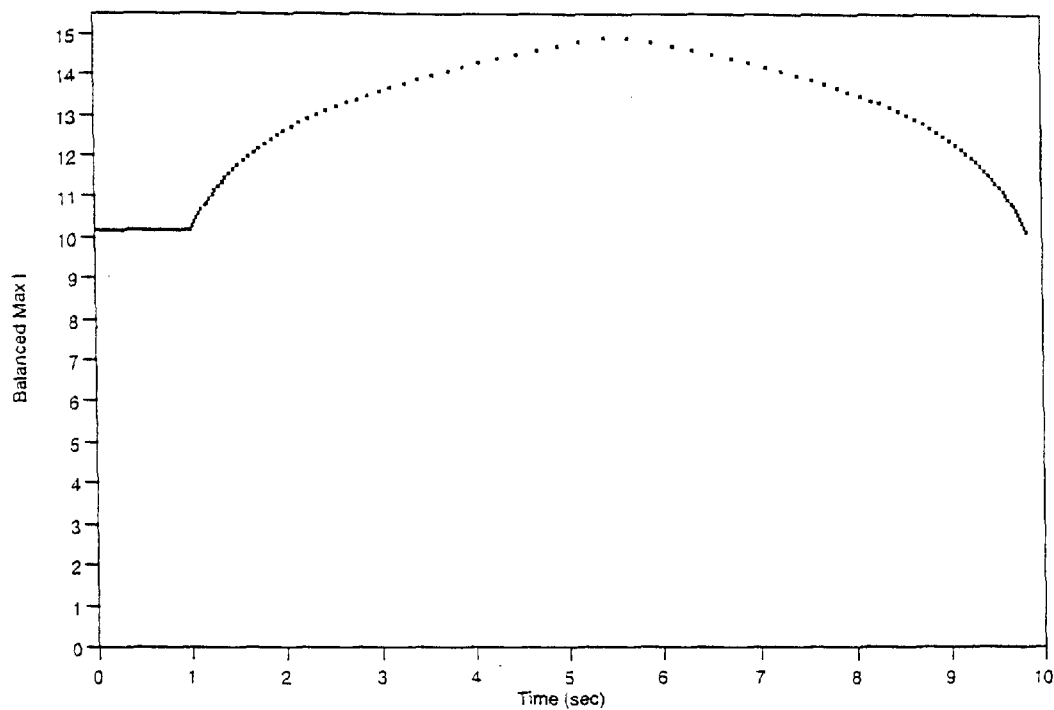
FIG. 7 is a plot illustrating the resulting electrical signal pulse amplitude versus time when the electrical signal pulse amplitude is varied with frequency as illustrated in FIG. 6.

The resulting current adjustment is illustrated in FIG. 7. It is of course understood that a therapy cycle should exceed 10 seconds and that the frequency and amplitude pattern illustrated in FIGS. 5 and 7 would be repeated until the therapy session is completed.

Figure 8:
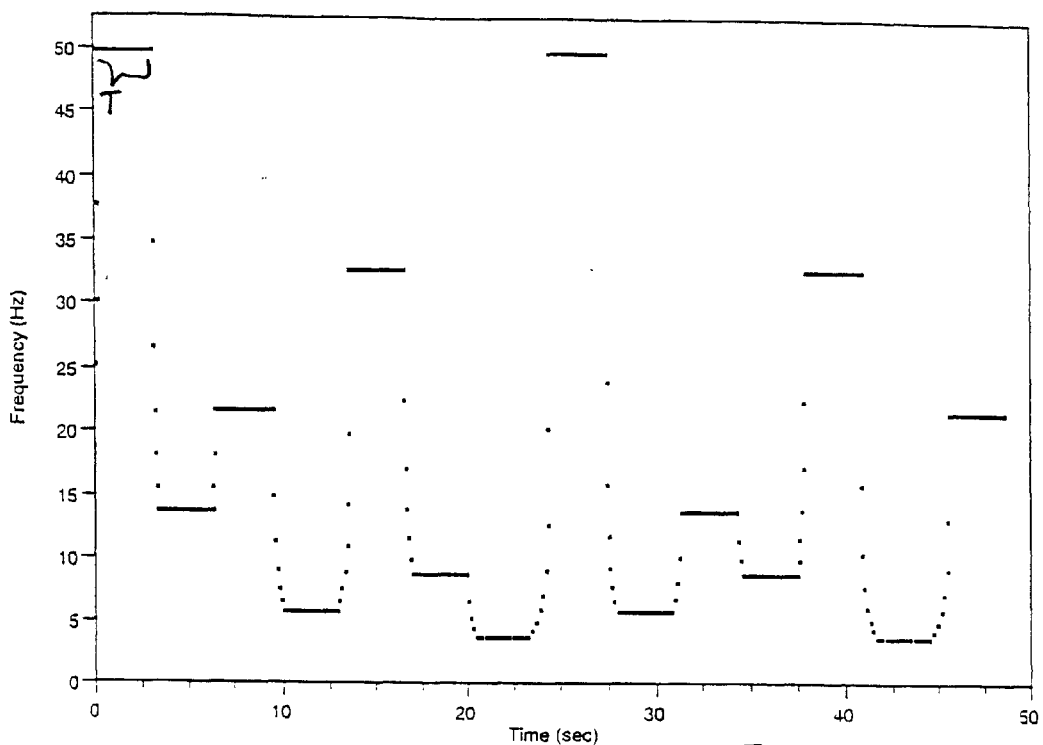
FIG. 8 is a plot illustrating the manner in which the electrical signal frequency may be randomly varied with time in accordance with another embodiment of the present invention.

FIG. 8 shows another manner in which the frequency of the electrical signal may be varied over time. Again, the electrical signal dwells at the upper limit for an initial time T and then thereafter varies randomly within the selected frequency range. With each adjustment in frequency, the frequency, and hence the IPI is held constant for a few seconds. During each adjustment in frequency, the IPT varies monotonically between the previously selected frequency and the newly selected frequency.

Figure 9:
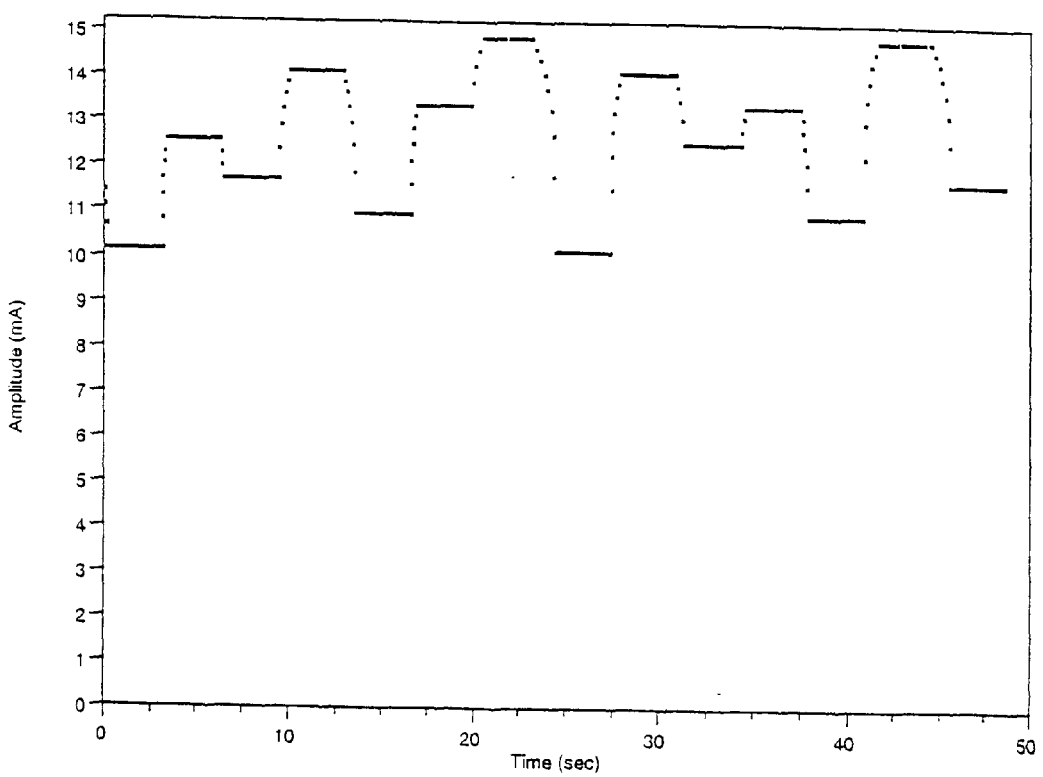
FIG. 9 is a plot illustrating the resulting electrical signal pulse amplitude versus time when the electrical signal amplitude is varied with frequency as illustrated in FIG. 6.

FIG. 9 shows the current amplitude versus time for the electrical signal represented in FIG. 8 wherein the current is adjusted in accordance with the relationship to frequency as described with respect to FIG. 6. As those skilled in the art would appreciate, either the current amplitude or the voltage amplitude may be adjusted.

Figure 10:
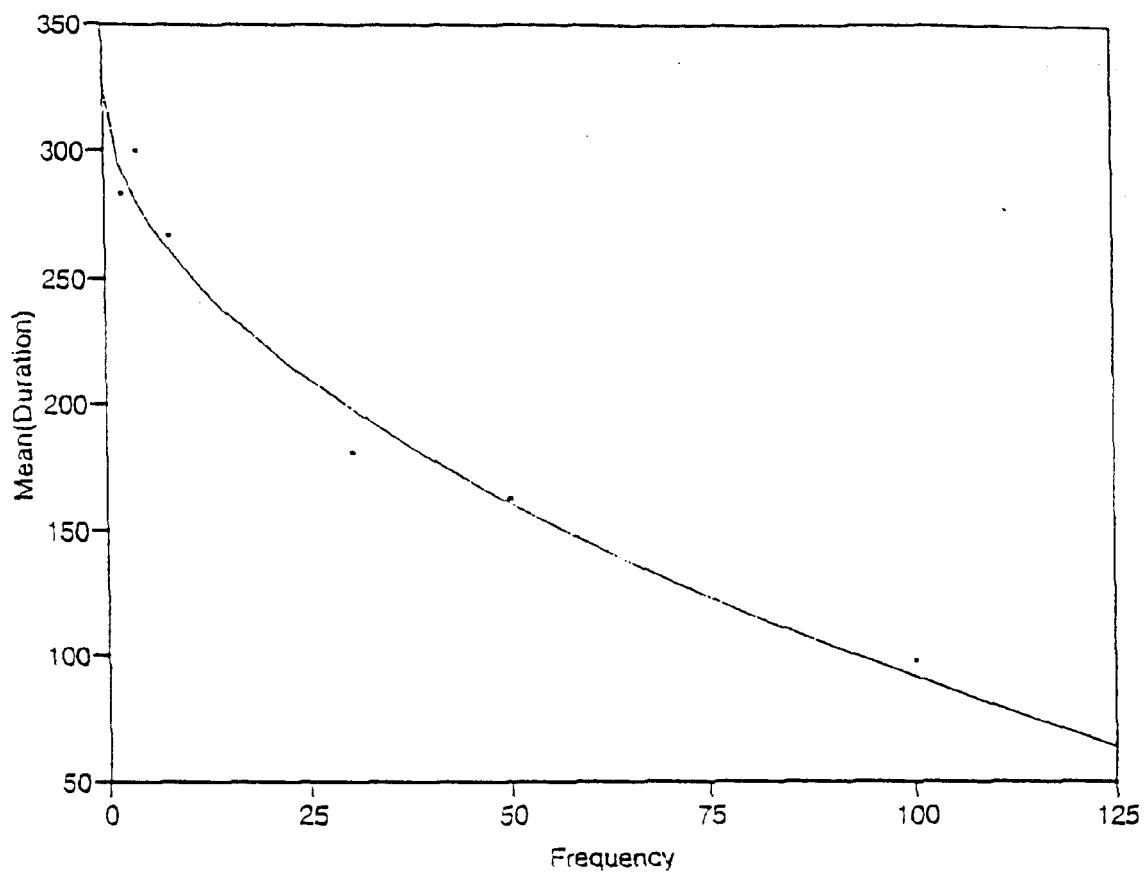
FIG. 10 is a plot illustrating the manner in which the electrical signal pulse width may be varied with frequency in accordance with a further embodiment of the present invention.

FIG. 10 shows the compensation made to the electrical signal represented in FIG. 5 wherein the total pulse duration (TD) is varied with frequency instead of the amplitude. The relationship is adjustment in total pulse duration in accordance with the formula:

$$TD = C_1 - C_2 \sqrt{F}$$

wherein, $C_1$ and $C_2$ are constants, and

F is the frequency of the electrical signal.

As those skilled in the art will appreciate, both amplitude and duration may be varied together to achieve the desired electrical signal compensation with frequency.

As may thus be seen from the foregoing, the present invention provides a new and improved system and method for treating a patient with electrical therapy. In accordance with the broader aspects of the present invention, the frequency of the applied electrical signal is automatically varied over a range of therapeutic effectiveness. Thus, there is no need for trial and error in adjusting pulse frequencies for a given patient. Further, a broad range of caregivers may use the system with minimal medical training and provide effective therapy for a large patient population.

In addition, the present invention overcomes the problem with patients becoming physiologically adapted to single or a limited number of frequencies. Still further, in addition to overcoming physiologic adaptation, the present invention provides a therapy that is not perceived as psychologically mundane, a common patient perception when receiving a constant stimulus for a typical treatment session of 30 minutes.

In accordance with further aspects of the present invention, the present invention provides for the automatic adjustment of the energy delivered with frequency. This renders the therapy optimal across the entire frequency range.

While particular embodiments of the present invention have been shown and described, modifications may be made, and it is therefore intended to cover in the appended claims all such changes and modifications which fall within the true spirit and scope of the invention.

What is claimed:

1. A method of providing percutaneous electrical therapy to a patient having a body, the method comprising:
   percutaneously inserting an electrode into the patient; and
   applying an electrical signal between the electrode and the patient's body at a plurality of frequencies that automatically vary over a range having a minimum frequency of at most about 20 Hz and having a maximum frequency of at least about 40 Hz.

2. The method of claim 1 wherein applying the electrical signal comprises applying an electrical signal between the electrode and the patient's body at a plurality of frequencies that automatically vary over a range having a minimum frequency of at most about 4 Hz and having a maximum frequency of at least about 50 Hz.

3. The method of claim 1 wherein applying the electrical signal comprises applying an electrical signal between the electrode and the patient's body at a plurality of frequencies that automatically vary over a range having a minimum frequency of at most about 2 Hz and having a maximum frequency of at least about 100 Hz.

4. The method of claim 1 wherein applying the electrical signal comprises applying an electrical signal between the electrode and the patient's body at a plurality of frequencies that automatically vary over a range having a minimum frequency of at most about 2 Hz and having a maximum frequency of at least about 200 Hz.

5. The method of claim 1 wherein the plurality of frequencies comprises more than seven frequencies.

6. The method of claim 1 wherein the electrical signal comprises a plurality of pulses, each consecutive pair of pulses being separated by an interpulse interval.

7. The method of claim 6 wherein the interpulse interval of at least a portion of the electrical signal varies with each pulse.

8. The method of claim 6 wherein successive interpulse intervals of at least a portion of the electrical signal vary in a predetermined manner.

9. The method of claim 6 wherein successive interpulse intervals of at least a portion of the electrical signal vary monotonically.

10. The method of claim 9 wherein the successive interpulse intervals of at least a portion of the electrical signal increase monotonically.

11. The method of claim 9 wherein the successive interpulse intervals of at least a portion of the electrical signal decrease monotonically.

12. The method of claim 6 wherein successive interpulse intervals of at least a portion of the electrical signal vary randomly.

13. The method of claim 6 wherein successive interpulse intervals of at least a portion of the electrical signal vary in a randomly generated and repeated manner.

14. The method of claim 6 wherein successive interpulse intervals of at least a portion of the electrical signal are constant.

15. The method of claim 6 wherein successive interpulse intervals of multiple portions of the electrical signal are constant.

16. The method of claim 6 wherein the pulse is a biphasic pulse.

17. The method of claim 1, further comprising compensating the electrical signal for changes in frequency of the electrical signal.

18. The method of claim 17 wherein compensating the electrical signal comprises adjusting the amplitude of the electrical signal in relation to the frequency of the electrical signal.

19. The method of claim 18 wherein adjusting the amplitude includes adjusting the amplitude of the electrical signal in an inverse relation to the frequency of the electrical signal.

20. The method of claim 18 wherein adjusting the amplitude includes adjusting the amplitude of the electrical signal in inverse relation to the log of the frequency of the electrical signal.

21. The method of claim 18 wherein adjusting the amplitude includes adjusting the amplitude (A) of the electrical signal in accordance with the formula:

$$A = C_1 - C_2 \log(F)$$

wherein,
   $C_1$ and $C_2$ are constants, and
   F is the frequency of the electrical signal.

22. The method of claim 18 wherein adjusting the amplitude comprises adjusting the amplitude of current of the electrical signal in relation to the frequency of the electrical signal.

23. The method of claim 18 wherein adjusting the amplitude comprises adjusting the amplitude of voltage of the electrical signal in relation to the frequency of the electrical signal.

24. The method of claim 17 wherein compensating the electrical signal comprises adjusting the duration of pulses comprising the electrical signal.

25. The method of claim 24 wherein adjusting the duration of pulses includes adjusting the duration of the pulses in an inverse relation to the frequency of the electrical signal.

26. The method of claim 24 wherein adjusting the duration of pulses includes adjusting the duration of the pulses in inverse relation to the square root of the frequency of the electrical signal.

27. The method of claim 24 wherein adjusting the duration of pulses includes adjusting the duration of the pulses in accordance with the formula:

$$TD = C_1 - C_2 \sqrt{F}$$

wherein,
   $C_1$ and $C_2$ are constants, and
   F is the frequency of the electrical signal.

28. A system for providing percutaneous electrical therapy to a patient having a body, the system comprising:
   electrode means percutaneously insertable into the patient; and
   signal generating means for applying an electrical signal between the electrode means and the patient's body, the signal generating means including frequency varying means for applying the electrical signal between the electrode means and the patient's body at a plurality of frequencies that automatically vary over a range having a minimum frequency of at most about 20 Hz and having a maximum frequency of at least about 40 Hz.

29. The system of claim 28 wherein the frequency varying means includes means for applying the electrical signal between the electrode and the patient's body at a plurality of frequencies that automatically vary over a range having a minimum frequency of at most about 4 Hz and having a maximum frequency of at least about 50 Hz.

30. The system of claim 28 wherein the frequency varying means includes means for applying the electrical signal between the electrode and the patient's body at a plurality of frequencies that automatically vary over a range having a minimum frequency of at most about 2 Hz and having a maximum frequency of at least about 100 Hz.

31. The system of claim 28 wherein the frequency varying means includes means for applying the electrical signal between the electrode and the patient's body at a plurality of frequencies that automatically vary over a range of at most about 2 Hz to at least about 200 Hz.

32. The system of claim 28 wherein the plurality of frequencies comprises more than seven frequencies.

33. The system of claim 28 wherein the electrical signal comprises a plurality of pulses, each consecutive pair of pulses being separated by an interpulse interval.

34. The system of claim 33 wherein the frequency varying means varies the interpulse interval of at least a portion of the electrical signal with each pulse.

35. The system of claim 33 wherein the frequency varying means varies interpulse intervals of at least a portion of the electrical signal in a predetermined manner.

36. The system of claim 33 wherein the frequency varying means varies successive interpulse intervals of at least a portion of the electrical signal monotonically.

37. The system of claim 36 wherein the frequency varying means increases successive interpulse intervals of at least a portion of the electrical signal monotonically.

38. The system of claim 36 wherein the frequency varying means decreases successive interpulse intervals of at least a portion of the electrical signal monotonically.

39. The system of claim 33 wherein the frequency varying means randomly varies successive interpulse intervals of at least a portion of the electrical signal.

40. The system of claim 33 wherein the frequency varying means varies successive interpulse intervals of at least a portion of the electrical signal in a randomly generated and repeated manner.

41. The system of claim 33 wherein the frequency varying means maintains successive interpulse intervals of at least a portion of the electrical signal constant.

42. The system of claim 33 wherein the frequency varying means maintains successive interpulse intervals of multiple portions of the electrical signal constant.

43. The system of claim 33 wherein the pulse is a biphasic pulse.

44. The system of claim 28 further including compensating means for compensating the electrical signal for changes in frequency of the electrical signal.

45. The system of claim 44 wherein the compensating means adjusts the amplitude of the electrical signal in relation to the frequency of the electrical signal.

46. The system of claim 44 wherein the compensating means adjusts the amplitude of the electrical signal in an inverse relation to the frequency of the electrical signal.

47. The system of claim 44 wherein the compensating means adjusts the amplitude of the electrical signal in inverse relation to the log of the frequency of the electrical signal.

48. The system of claim 44 wherein the compensating means adjusts the amplitude (A) of the electrical signal in accordance with the formula:

$$A = C_1 - C_2 \log(F)$$

wherein, $C_1$ and $C_2$ are constants, and

F is the frequency of the electrical signal.

49. The system of claim 46 wherein the compensating means adjusts the amplitude of the electrical signal in relation to the frequency of the electrical signal.

50. The system of claim 46 wherein the compensating means adjusts the amplitude of the voltage of the electrical signal in relation to the frequency of the electrical signal.

51. The system of claim 44 wherein the compensating means adjusts duration of pulses comprising the electrical signal.

52. The system of claim 44 wherein the compensating means adjusts the duration of the pulses in an inverse relation to the frequency of the electrical signal.

53. The system of claim 44 wherein the compensating means adjusts the duration of the pulses in inverse relation to the square root of the frequency of the electrical signal.

54. The system of claim 44 wherein the compensating means adjusts the duration of the pulses in accordance with the formula:

$$TD = C_1 - C_2 \sqrt{F}$$

wherein, $C_1$ and $C_2$ are constants, and

F is the frequency of the electrical signal.

55. A system for providing percutaneous electrical therapy to a patient having a body, the system comprising:

at least one electrode percutaneously insertable into the patient; and a signal generator adapted to be coupled between the at least one electrode and the patient's body and that generates an electrical signal at a plurality of frequencies that automatically vary over a range of frequencies having a minimum frequency of at most about 20 Hz and having a maximum frequency of at least about 40 Hz.

56. The system of claim 55 wherein the signal generator varies the electrical signal over a range of frequencies having a minimum frequency of at most about 4 Hz and having a maximum frequency of at least about 50 Hz.

57. The system of claim 55 wherein the signal generator varies the electrical signal over a range of frequencies having a minimum frequency of at most about 2 Hz and having a maximum frequency of at least about 100 Hz.

58. The system of claim 55 wherein the signal generator varies the electrical signal over a range of frequencies of at most about 2 Hz to at least about 200 Hz.

59. The system of claim 55 wherein the plurality of frequencies comprises more than seven frequencies.

60. The system of claim 55 wherein the signal generator generates the electrical signal by generating a plurality of pulses and separating each consecutive pair of pulses by an interpulse interval.

61. The system of claim 60 wherein the signal generator varies the interpulse interval after each pulse of at least a portion of the electrical signal.

62. The system of claim 60 wherein the signal generator varies the interpulse intervals of at least a portion of the electrical signal in a predetermined manner.

63. The system of claim 60 wherein the signal generator varies successive interpulse intervals of at least a portion of the electrical signal monotonically.

64. The system of claim 63 wherein the signal generator increases successive interpulse intervals of at least a portion of the electrical signal monotonically.

65. The system of claim 63 wherein the signal generator decreases successive interpulse intervals of at least a portion of the electrical signal monotonically.

66. The system of claim 60 wherein the signal generator randomly varies successive interpulse intervals of at least a portion of the electrical signal.

67. The system of claim 60 wherein the signal generator varies successive interpulse intervals of at least a portion of the electrical signal in a randomly generated and repeated manner.

68. The system of claim 60 wherein the signal generator maintains successive interpulse intervals of at least a portion of the electrical signal constant.

69. The system of claim 60 wherein the signal generator maintains successive interpulse intervals of multiple portions of the electrical signal constant.

70. The system of claim 60 wherein the pulses generated by the signal generator are biphasic pulses.

71. The system of claim 55 wherein the signal generator adjusts the electrical signal for changes in frequency of the electrical signal.

72. The system of claim 71 wherein the signal generator adjusts the amplitude of the electrical signal in relation to the frequency of the electrical signal.

73. The system of claim 71 wherein the signal generator adjusts the amplitude of the electrical signal in an inverse relation to the frequency of the electrical signal.

74. The system of claim 71 wherein the signal generator adjusts the amplitude of the electrical signal in inverse relation to the log of the frequency of the electrical signal.

75. The system of claim 71 wherein the signal generator adjusts the amplitude (A) of the electrical signal in accordance with the formula:

$$A = C_1 - C_2 \log(F)$$

wherein,
$C_1$ and $C_2$ are constants, and
F is the frequency of the electrical signal.

76. The system of claim 73 wherein the signal generator adjusts the amplitude of the current of the electrical signal in relation to the frequency of the electrical signal.

77. The system of claim 73 wherein the signal generator adjusts the amplitude of the voltage of the electrical signal in relation to the frequency of the electrical signal.

78. The system of claim 71 wherein the signal generator adjusts duration of the pulses comprising the electrical signal for changes in frequency of the electrical signal.

79. The system of claim 71 wherein the signal generator adjusts the duration of the pulses in an inverse relation to the frequency of the electrical signal.

80. The system of claim 71 wherein the signal generator adjusts the duration of the pulses in inverse relation to the log of the frequency of the electrical signal.

81. The system of claim 71 wherein the signal generator adjusts the duration of the pulses in accordance with the formula:

$$TD = C_1 - C_2 \sqrt{F}$$

wherein,
$C_1$ and $C_2$ are constants, and
F is the frequency of the electrical signal.

* * * * *